United States Patent
Frigoli et al.

(10) Patent No.: US 7,553,978 B2
(45) Date of Patent: Jun. 30, 2009

(54) PROCESS FOR THE PREPARATION OF 1-NAPHTHOL MIXED ETHERS AND INTERMEDIATES OF CRYSTALLINE FORMS OF (+) AND (−)-DULOXETINE

(75) Inventors: Samuele Frigoli, Garbagnate Milanese (IT); Claudio Fuganti, Garbagnate Milanese (IT); Roberta Pizzocaro, Garbagnate Milanese (IT)

(73) Assignee: Solmag S.p.A., Mulazzano (IT)

( * ) Notice: Subject to any disclaimer, the term of this patent is extended or adjusted under 35 U.S.C. 154(b) by 0 days.

(21) Appl. No.: 12/090,619

(22) PCT Filed: Oct. 13, 2006

(86) PCT No.: PCT/EP2006/009912

§ 371 (c)(1),
(2), (4) Date: Jul. 21, 2008

(87) PCT Pub. No.: WO2007/045405

PCT Pub. Date: Apr. 26, 2007

(65) Prior Publication Data

US 2008/0287693 A1    Nov. 20, 2008

(30) Foreign Application Priority Data

Oct. 18, 2005    (IT)    .......................... MI2005A1970

(51) Int. Cl.
*C07D 333/20*    (2006.01)

(52) U.S. Cl. ........................................ 549/75
(58) Field of Classification Search ................ 549/75
See application file for complete search history.

(56) References Cited

FOREIGN PATENT DOCUMENTS

EP    0 273 658 B1    10/1990

*Primary Examiner*—Bernard Dentz
*Assistant Examiner*—David E Gallis
(74) *Attorney, Agent, or Firm*—Arent Fox LLP

(57) ABSTRACT

The invention relates to a process for the preparation of duloxetine (1a), comprising the reaction between 1-fluoronaphthalene and 3-N,N-dimethylamino-1-(2-thienyl)-propan-1-ol in the presence of 1,3-dimethyl-2-oxo-hexahydropyrimidine (DMPU) as the solvent; a method for the identification of duloxetine enantiomers and for the determination of its optical purity is also disclosed.

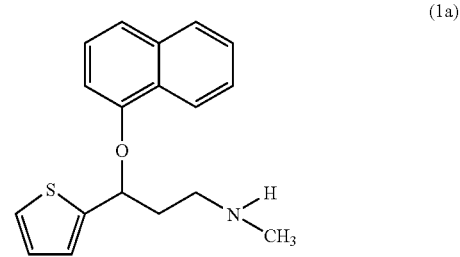

(1a)

1 Claim, No Drawings

PROCESS FOR THE PREPARATION OF 1-NAPHTHOL MIXED ETHERS AND INTERMEDIATES OF CRYSTALLINE FORMS OF (+) AND (−)-DULOXETINE

CROSS-REFERENCE TO RELATED APPLICATION

This application is a National Stage entry of International Application No. PCT/EP2006/009912, filed Oct. 13, 2006, the entire specification and claims of which are incorporated herewith by reference.

FIELD OF THE INVENTION

The present invention relates to a process for the preparation of 1-naphthol mixed ethers, in particular of duloxetine 1a:

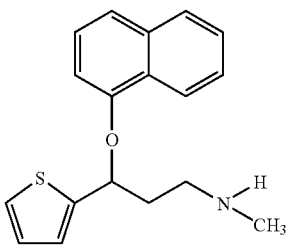

BACKGROUND OF THE INVENTION

The preparation of 1-naphthol mixed ethers raises remarkable interest, since it regards, for example, the synthesis of duloxetine 1a ((+)-(S)—N-methyl-γ-(1-naphthalenyloxy)-2-thiophenepropanamine), whose hydrochloride salt is used as antidepressant. EP 273 658 discloses two methods for the preparation of duloxetine or of its precursor 1b:

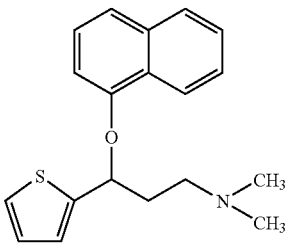

A first procedure comprises the use of 1-naphthol 3a

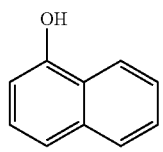

and of compounds of formula 2.

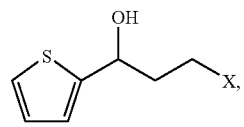

in particular compound 2a in which X=N(CH$_3$)$_2$.

The ether bond in compounds 1a and 1b forms through Mitsunobu reaction, which consists in the treatment in a ether solvent, for example tetrahydrofuran, of compounds 3a and 2 with equimolecular amounts of triphenylphosphine and of an azodicarboxylic acid ester (typically the diisopropyl ester). In this way the ether bond forms with inversion of configuration, obtaining as by-products equimolecular amounts of triphenylphosphine oxide and diisopropyl hydrazodicarboxylate, whose separation from the desired ether is troublesome. The X substituent in compounds 2 can be, further to —N(CH$_3$)$_2$, any good leaving group susceptible of being substituted with a nitrogen function which allows to obtain (+)-duloxetine 1a. The Mitsunobu reaction with compound 2a proceeds in more than 24 h. The equimolar ratio of the two reagents (triphenylphosphine and azodicarboxylate) with respect to compounds 2 and 3a and the prolonged reaction times make this synthetic procedure not very profitable, even if it proceeds with inversion of configuration at the oxygen-bearing carbon in compounds 2.

A method for the synthesis of duloxetine 1a that is preferred to the one reported above envisages the use of 1-fluoronaphthalene 3b

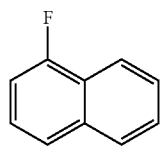

and 2a as substrates. Compound 2a is converted to the corresponding alkoxide by treatment with a strong base, for example NaH; the alkoxide replaces the fluorine at position 1 of 3b, leading to 1b. The substitution reaction of the fluorine on the aromatic ring is a particular reaction which involves an ionic intermediate (Meisenheimer intermediate) and which occurs, according to the state of the art, in N,N-dimethylacetamide and dimethylsulfoxide. When NaH is used as the base in DMSO, a temperature of 60-70° C. must not be exceeded. In particular, according to EP 273 658, compound 1b is obtained from 3b and 2a in N,N-dimethylacetamide, by treatment of 2 with sodium hydride, at a temperature of 70° C., to produce the alkoxide, followed by addition of 1-fluoronaphthalene 3b in equimolecular amount, heating at 110° C. for 60 min. The desired product 1b is recovered as crystalline oxalate in 76% yield.

DISCLOSURE OF THE INVENTION

It has now been found that the synthesis of duloxetine, in particular of its precursor 1b, can be carried out more conveniently from compounds 2 and 3b, if 1,3-dimethyl-2-oxo-hexahydropyrimidine (DMPU) is used as the solvent instead of dimethylacetamide.

Accordingly, the invention relates to a process for the preparation of duloxetine 1a:

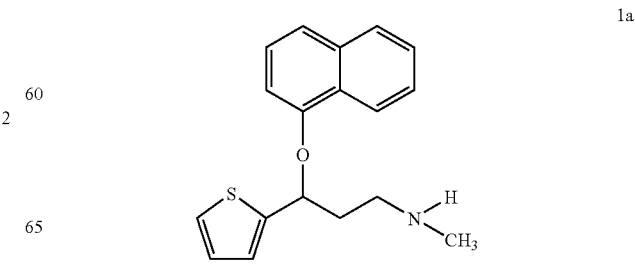

which comprises the reaction between 1-fluoronaphthalene 3b

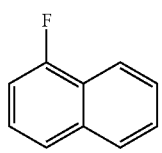

and 3-N,N-dimethylamino-1-(2-thienyl)-propan-1-ol 2a

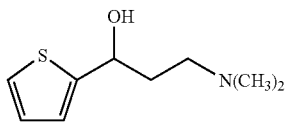

to give ((+)-(S)—N,N-dimethyl-γ-(1-naphthalenyloxy)-2-thiophenepropanamine) 1b:

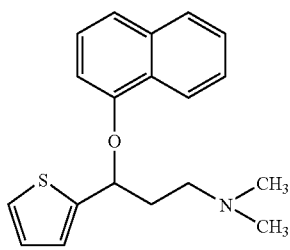

and the conversion of 1b to duloxetine 1a, characterized in that the reaction between 2a and 3b is carried out in 1,3-dimethyl-2-oxo-hexahydropyrimidine (DMPU) as the solvent.

Typically, the reaction takes place at a temperature ranging from 70 to 120° C., for a time ranging from 45 min. to 8 hours.

Comparative experiments for the synthesis of 1b from 1-fluoronaphthalene 3b and 3-N,N-dimethylamino-1-(2-thienyl)-propan-1-ol 2a, carried out using DMPU and dimethylacetamide as solvents, proved that DMPU is economically more advantageous than dimethylacetamide, as it requires lower reaction temperatures, shorter reaction times and provides higher yields.

Typically, compound 1b is recovered as the oxalate, which is subsequently hydrolysed and subjected to fractional crystallization with tartaric acid; compound 1b is recovered again by hydrolysis and each enantiomer is demethylated to give duloxetine 1a. Duloxetine enantiomers are also separated by fractional crystallization of the respective oxalates, hydrolysis of the salts, conversion to hydrochloride and recrystallization from ethanol.

The invention is illustrated in greater detail in the following experimental section.

EXPERIMENTAL SECTION

1. Comparative Experiments

Synthesis of (+)-(S)—N,N-dimethyl-γ-(1-naphthalenyloxy)-2-thiophenepropanamine) 1b either in dimethylacetamide or DMPU Sodium hydride was suspended in either dimethylacetamide or DMPU in a slight molar excess with respect to alcohol 2a, which was added under stirring and nitrogen atmosphere. The mixture was heated to 70° C. for 30 min., thereafter 1-fluoronaphthalene 3b was slowly added, keeping again under stirring and nitrogen atmosphere, then the temperature was raised and maintained at 80 or 100° C. for the required time. After that, the mixture was cooled to room temperature, added with a few ml of ethanol to destroy any excess of NaH and poured in 2 volumes of ice, followed by three extractions with 2 volumes of ethyl ether. The ether phase was washed three times with 1 volume of water and once with a saturated NaCl solution. After drying over sodium sulfate, the solvent was evaporated off and the oily residue was taken up in three volumes of methanol and added in the cold with 1.3 molar equiv. of oxalic acid in methanol. The resulting mixture was evaporated to dryness and the solid residue was crystallized from either hot methanol or ethyl acetate/methanol. The crystalline oxalate recovered by filtration was dried and weighed.

1b Oxalate: $^1$H NMR (DMSO-$d_6$) δ (8.27 (1H, m), 7.85 (1H, m), 7.53 (2H, m), 7.44 (2H, m), 7.33 (1H, t, J=7.9 Hz), 7.25 (1H, d, J=3.4 Hz), 7.04 (1H, d, J=7.7 Hz), 6.99 (1H, dd, J=3.5, 5.0 Hz), 6.02 (1H, dd, J=4.9, 7.7 Hz), 3.25 (1H, m), 3.15 (1H, m), 2.70 (6H, s), 2.58 (1H, m), 2.39 (1H, m).

The experiments were followed over time through GC/MS analysis of sample aliquots and the yield was determined on the weight of 1b oxalate recovered in crystalline pure form after completion of the reaction.

In particular, we calculated the yields in 1b resulting from the addition of 1.05 mol equiv. of 1-fluoronaphthalene 3b to 2a sodium salt, that had been obtained with 1.1 mols equiv. of NaH (60% suspension in oil) in DMPU and dimethylacetamide respectively at 70° C. for 30 min.

The results are reported hereinbelow.

1) At 100° C. and with 2% of 2a in DMPU, 2a completely disappeared after 50 min. and 1b as crystalline oxalate was obtained in 84% yield, whereas in dimethylacetamide after the same time 13% of 2a remained unreacted and the reaction terminated with complete disappearance of 2a (which is the limiting substrate) after 180 min.

2) At 100° C. and with 10% of 2a in DMPU, 3% of 2a remained unreacted after 50 min., whereas in dimethylacetamide the percentage of unreacted 2a was 14%. The reaction was complete in DMPU after 90 min. and in dimethylacetamide after 300 min. (2a concentration lower than 1%).

3) At 80° C. and with 2% of 2a in DMPU 2a completely disappeared after 50 min. and oxalate 1b was obtained in 85% yield, whereas in dimethylacetamide 4% of 2a was still unreacted after 300 min. If the reaction is interrupted at this time, the resulting oxalate 1b is contaminated by 2a. The separation of oxalates 2a and 1b through fractional crystallization is difficult and involves remarkable losses. In the present case, the reaction crude from this experiment led to oxalate 1b with a content in 2a lower than 0.5% after 3 crystallizations from ethyl acetate/methanol and with a final yield of 48%.

It is therefore of the utmost importance that upon completion of the reaction 1b is free from 2a, because the purification of the oxalates by fractional crystallization involves a remarkable decrease in yields.

2. Synthesis of (+) and (−)-duloxetine 1a (+) And (−)-duloxetine 1a were obtained from racemic oxalate 1b according to a known method, hydrolysing 1b base from the oxalate by treatment with an excess of aqueous NaOH and extraction of the free base with ethyl ether. The free base was combined respectively with a non-natural and natural form of tartaric acid to give, after three crystallizations of the crystalline salt from absolute ethanol, the salts of (+) and (−) 1a. The free bases were recovered by treatment with an excess of aqueous base and extraction with an ether solvent. N-demethylation of (+) and (−) 1b was carried out by treatment with phenyl chloroformate in toluene under reflux and subsequent basic hydrolysis in a high-boiling solvent. (+) And (−)-duloxetine 1a were purified by crystallization of the corresponding oxalates and the free bases obtained as described above were converted to hydrochlorides by treatment with gaseous HCl in ethanol. The solutions were evaporated to dryness and the residue was crystallized from boiling ethanol. The enantiomeric excess of the products, determined by HPLC on a Chiracel OD column (hexane/isopropanol/triethylamine) was higher than 99.9%.

(+)-1a hydrochloride: $^1$H NMR (DMSO-$d_6$) δ (8.26 (1H, m), 7.85 (1H, m), 7.52 (2H, m), 7.45 (2H, m), 7.34 (1H, t, J=8.0 Hz), 7.26 (1H, d, J=3.2 Hz), 7.06 (1H, d, J=7.6 Hz), 6.98 (1H, dd, J=3.7, 4.8 Hz), 6.14 (1H, dd, J=5.6, 7.3 Hz), 3.07 (2H, m), 2.55 (4H, m+s), 2.39 (1H, m); $[\alpha]_D^{20}$=+121 (c 1.00, methanol).

The invention claimed is:

1. A process for the preparation of duloxetine 1a:

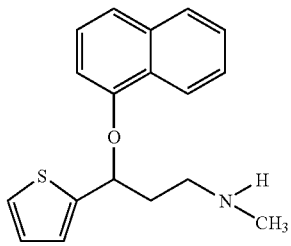

1a comprising the reaction between 1-fluoronaphthalene 3b

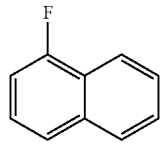

3b and 3-N,N-dimethylamino-1-(2-thienyl)-propan-1-ol 2a

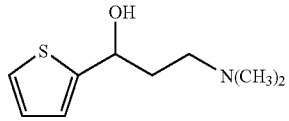

2a to give ((+)-(S)—N,N-dimethyl-γ-(1-naphthalenyloxy)-2-thiophenepropanamine) 1b:

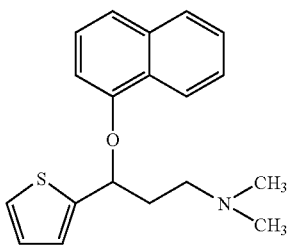

1b and the conversion of 1b to duloxetine 1a, characterized in that the reaction between 2a and 3b is carried out in 1,3-dimethyl-2-oxo-hexahydropyrimidine as the solvent.

* * * * *